United States Patent [19]

Hayakawa et al.

[11] Patent Number: 5,257,532

[45] Date of Patent: Nov. 2, 1993

[54] METHOD AND APPARATUS FOR MEASURING MOISTURE CONTENT AS A FUNCTION OF THERMAL RESPONSE

[75] Inventors: Kan-ichi Hayakawa, Princeton; Jian-Jun Wang, Piscataway, both of N.J.

[73] Assignee: Rutgers, The State University of New Jersey, New Brunswick, N.J.

[21] Appl. No.: 905,459

[22] Filed: Jun. 29, 1992

[51] Int. Cl.$^5$ .......................................... G01N 25/56
[52] U.S. Cl. ..................................... 73/75; 364/556; 374/45; 73/863.11
[58] Field of Search .................. 73/75, 863.11, 864.91; 374/45; 364/556, 499

[56] References Cited

U.S. PATENT DOCUMENTS

| | | | |
|---|---|---|---|
| 3,216,241 | 11/1965 | Hansen | 73/75 |
| 3,757,206 | 9/1973 | Dorst | 324/32 |
| 4,165,633 | 8/1979 | Raisanen | 73/76 |
| 4,310,758 | 1/1982 | Peterson | 250/255 |
| 4,399,404 | 8/1983 | Resh | 324/61 |
| 4,532,797 | 8/1985 | Yang | 73/75 |
| 4,546,645 | 10/1985 | Delmulle et al. | 73/74 |
| 4,568,875 | 2/1986 | Piso et al. | 324/669 |
| 4,612,802 | 9/1986 | Clarke et al. | 374/45 |
| 4,651,285 | 3/1987 | Collins et al. | 364/496 |
| 4,774,831 | 10/1988 | Nordin | 374/45 |
| 4,845,978 | 7/1989 | Whitford | 73/75 |
| 4,864,850 | 9/1989 | Price | 73/73 |
| 5,042,294 | 8/1991 | Uzzell | 73/75 |

FOREIGN PATENT DOCUMENTS 0800846  1/1981  U.S.S.R. .................................. 73/75

OTHER PUBLICATIONS

J. Wang et al., "Thermal Conductivity of Foods at High Temperatures as Influenced By Moisture Content," 8-page copy of talk at R&D Associates, Boston, Mass., (Oct. 1991).

E. G. Murakami et al., "Measurement and Prediction of Thermal Properties of Foods," pp. 3–7, 12, 13, 15–26, Food Properties and Computer-Aided Engineering of Food Processing Systems, ed. by R. P. Singh et al., Kluwer Academic Pub., The Netherlands (1989).

L. van den Berg et al., "Effect of Composition on Thermal Properties of Fresh and Frozen Foods," pp. 79–83, Canadian Institute of Food Science and Technology Journal, vol. 8, No. 2 (1975).

K. Helrich (editor), "Official Methods of Analysis of The Association of Official Analytical Chemists," pp. 840–842, 931, 990 (1990).

J. E. Lozano et al., "Thermal Conductivity of Apples As a Function of Moisture Content," pp. 198–199, Journal of Food Science, vol. 44, No. 1 (1979).

V. E. Sweat, "Experiment Values of Thermal Conductivity of Selected Fruits and Vegetables," pp. 1080–1083, Journal of Food Science, vol. 39 (1974).

F. C. Hooper et al., "Transient Heat Flow Apparatus For The Determination of Thermal Conductivities," pp. 129–134, Heating, Piping & Air Conditioning, (Aug. 1950).

Primary Examiner—William A. Cuchlinski, Jr.
Assistant Examiner—Diego F. F. Gutierrez
Attorney, Agent, or Firm—Charles S. Phelan

[57] ABSTRACT

Moisture content measurements are accomplished as a function of temperature by measuring the temperature-difference versus natural-logarithm-of-heating-time response of a sample of a predetermined material during a predetermined interval of application of a predetermined quantity of heat, determining the slope of that response at a portion thereof of substantially maximum slope, determining the mean sample temperature through the duration of that response portion, and calculating the moisture content of the sample as a function of that slope and that mean temperature. A thermal probe is used for both applying controlled heat to a material sample and sensing resulting temperature changes within the sample. The probe includes a line heat source and either a thermocouple sensing element or a thermistor sensing element. Sample holders are employed which limit diversion of heat from the heater via paths other than through the sample material. In one embodiment the sample holder has an externally controllable internal volume to facilitate measurements by establishing a predetermined sample density.

24 Claims, 5 Drawing Sheets

METHOD AND APPARATUS FOR MEASURING MOISTURE CONTENT AS A FUNCTION OF THERMAL RESPONSE

FIELD OF THE INVENTION

This invention relates to the measurement of moisture content of materials, and it relates in particular to the measurement of the moisture content of materials such as liquids, semi-solids, and powders.

BACKGROUND OF THE INVENTION

In certain situations it is useful to make precise determinations of the moisture content of materials. The food processing industry is one which has such needs; and, for purposes of illustration, the present invention will be described in that environment.

In the food processing industry, governmental regulations often fix a stringent limit on the minimum or maximum amount of moisture that is permitted to be present in a given product. In all cases, it is desirable to be able conveniently to guide the composition of food materials as to moisture content in order that tight control of processing can be maintained to assure efficient operation and efficient use of resources.

Heretofore the moisture content of liquid, semi-solid, or powdered food material has been determined by a variety of methods, including, for example, a gravimetric method, utilizing either a vacuum or a microwave oven [i.e., Association of Official Analytical Chemists (AOAC) Method 1990. Both variations are inconvenient to use when regular measurement of the moisture content of, e.g., hundreds of samples is required. The vacuum oven variation further requires undesirably long measurement times for on-line food processing. Some other methods include measuring reflectance or absorption or some other parameter as an indirect indication of moisture content. However, all prior techniques have been found to lack at least one of several requirements for conveniently and meaningfully measuring moisture content of food materials. Such requirements include, illustratively, high temperature tolerance [e.g., up to about 120° C.], short time [preferably less than about five minutes] to make a moisture content measurement of a sample, ease of calibration, and substantially no contamination between sensor and food system.

It has long been known that moisture content has a strong influence on thermal conductivity of materials. This is shown, for example, in an F. C. Hooper et al. paper "Transient Heat Flow Apparatus for the Determination of Thermal Conductivities" which appeared in *Heating Piping & Air Conditioning*, Aug. 1950, pages 129–134. In Hooper et al., a probe containing a line heat source and thermocouple junctions was utilized to make temperature measurements in a variety of materials, including soil. Heating time used was short enough that moisture content of a sample did not change. Corrections were made for the finite diameter of the probe, and temperature and heating current were measured to three significant figures. Thermal conductivity was determined from the slope of the temperature rise in a sample versus the natural logarithm of heating time in the time interval between four and ten minutes after the start of heater current.

A number of workers have tried to correlate temperature response properties as a function of moisture content, but none has been able to satisfy all of the above mentioned requirements for use in food processing systems. Some examples of this type of work are noted below.

J. E. Lozano et al. reported in "Thermal Conductivity of Apples As A Function of Moisture Content," Journal of Food Science, Vol. 44, No. 1 (1979), pages 198–199, the measurement of temperature rise in respective apple samples having different known moisture contents. Each sample was heated for a known heating time and at a known level, and the thermal conductivity was calculated as a function of the measured temperature difference.

V. E. Sweat used a thermal probe to measure thermal conductivities of various fruits and vegetables in an effort to determine whether or not thermal conductivity could be estimated using water content and temperature of a sample. "Experimental Values of Thermal Conductivity of Selected Fruits and Vegetables," Journal of Food Science, Vol. 39 (1974), pages 1080–1083. The author concluded that there was a sufficient correlation between water content and thermal conductivity of certain fruits and vegetables that a linear regression equation could be used to predict thermal conductivity as a function of water content to within ±15%.

A U.S. Pat. No. 4,845,978 to D. R. Whitford discloses, for purposes of controlling an irrigation system, that the time rate of temperature rise in soil could be considered to be an approximate indication of moisture content in the soil. Whitford employed a thermal probe including a point heat source and a spatially separated temperature sensor. However, the technique requires heating for a much longer time interval than can be tolerated for most foods, especially those which must be processed at elevated temperatures ranging over 100° Celsius [C.]. Furthermore, a straight-line approximation of a temperature versus heating-time curve, such as taught in Whitford, has been found to lack sufficient precision for use in processing many food materials.

Several prior workers have exploited a relationship between moisture content and some parameter, other than temperature, by applying linear regression analysis to obtain moisture-related information about a sample. For example, a U.S. Pat. No. 4,310,758 to J. R. Peterson teaches the direct measurement of bidirectional reflectance factors as to spectral reflectance for soil and utilization of those data in predictive equations, determined from regression analysis, to solve for moisture tension (vis-a-vis moisture content). Similarly, a U.S. Pat. No. 4,568,875 to J. S. Piso et al. teaches the direct measurement of yarn denier and utilization of those data in certain equations determined with the aid of regression analysis to solve for moisture content of yarn samples having unknown moisture content. In yet another case, U.S. Pat. No. 4,651,285 to M. J. Collins et al., fat content of certain food materials is determined by measuring density and measuring solids content and utilizing that data in equations, determined by regression analysis, to solve for fat content of samples having unknown fat content. It is stated in Collins et al. that a measurement of moisture content can be employed instead of solids content, and presumably that statement is based upon a prior statement in the patent that it is known to determine moisture content by a gravimetric method including heating by microwave energy. None of the foregoing methods meets all of the requirements for conveniently and meaningfully determining moisture content of food materials.

Another problem associated with moisture content measurements based upon thermal characteristics of materials being measured is that heretofore sample material has been installed in a sample holder, and thereafter a thermal probe has been assembled into the holder. Since an operator is unable to monitor visually the probe-sample interface for the full extent of the probe length during probe installation, there can be undetected nonuniformities in the interface between the sample material and the probe. Such nonuniformities distort heat transfer across that interface and, therefore, the temperature measurements being made.

Yet another difficulty associated with moisture content measurement based upon thermal characteristics of materials being measured arises from the fact that the density of a powdered material sample is known to have a strong effect upon thermal response measurements. Known techniques such as, e.g., tapping a sample holder to cause the material to settle or gas injection to measure the extent of voids in the sample holder, are either lacking in precision [tapping] or unduly time consuming [gas injection].

SUMMARY OF THE INVENTION

The foregoing problems associated with moisture content measurements are alleviated by measuring the temperature-deference versus logarithm-of-heating-time response of a sample of a predetermined material during a predetermined heating time interval, determining the slope of that response at a portion thereof of approximately maximum slope, determining a temperature parameter related to the temperature at the start of heat application, and calculating the moisture content of the sample as a function of that slope and that temperature parameter.

It is preferred to employ a line heat source thermal probe both to heat a sample of a predetermined material being measured and to measure temperature rise in the sample over a predetermined heating interval at a predetermined rate of heat application. Probe apparatus is arranged substantially to limit the transfer of heat from the heat source to the sample material. An automated data collection and processing facility is optimized to employ state of the art components and techniques to enhance the accuracy of time measurements, heating application, and temperature measurements.

In applications where sample material is not characterized by an initial, substantially uniform temperature distribution, a sample holder is used to facilitate initial temperature stabilization. A first sample holder embodiment has a removable, sealing cover on each end of the cylinder, and the probe is removably mounted through the center of one of those covers. This permits the probe to be installed in the holder at one end and the sample material thereafter installed from the other end of the holder so that the holder filling can be closely visually monitored to assure uniform contact with the probe. The cover in which the probe is installed is made up of plural, concentric, threadedly engaging parts which permit the probe mounting to be accomplished in a center one of the parts which is then inserted into position to cover one end of the holder, with the probe extending into the interior of the holder. Then an outer part is thereafter applied over the edges of the first part for threadedly engaging the outer surface adjacent to the one end of the holder cylinder.

A second embodiment of the sample holder is similar in configuration and sealing to the first sample holder embodiment. This second embodiment includes at least one movable piston within the holder. The piston is externally driven, through the holder cover opposite to the one supporting the probe, to compact a material sample of known weight to a predetermined volume so that all samples for a given food type will have a predetermined density. A central longitudinal aperture is provided in the at least one piston, in the piston face toward the sample material, to receive the tip of the probe and thereby assure that the probe remains centered during compacting of the sample.

BRIEF DESCRIPTION OF THE DRAWINGS

A more complete understanding of the invention and its various features, objects, and advantages can be obtained from a consideration of the appended claims in conjunction with the following Detailed Description and the attached drawings in which:

DETAILED DESCRIPTION

Figure 1:
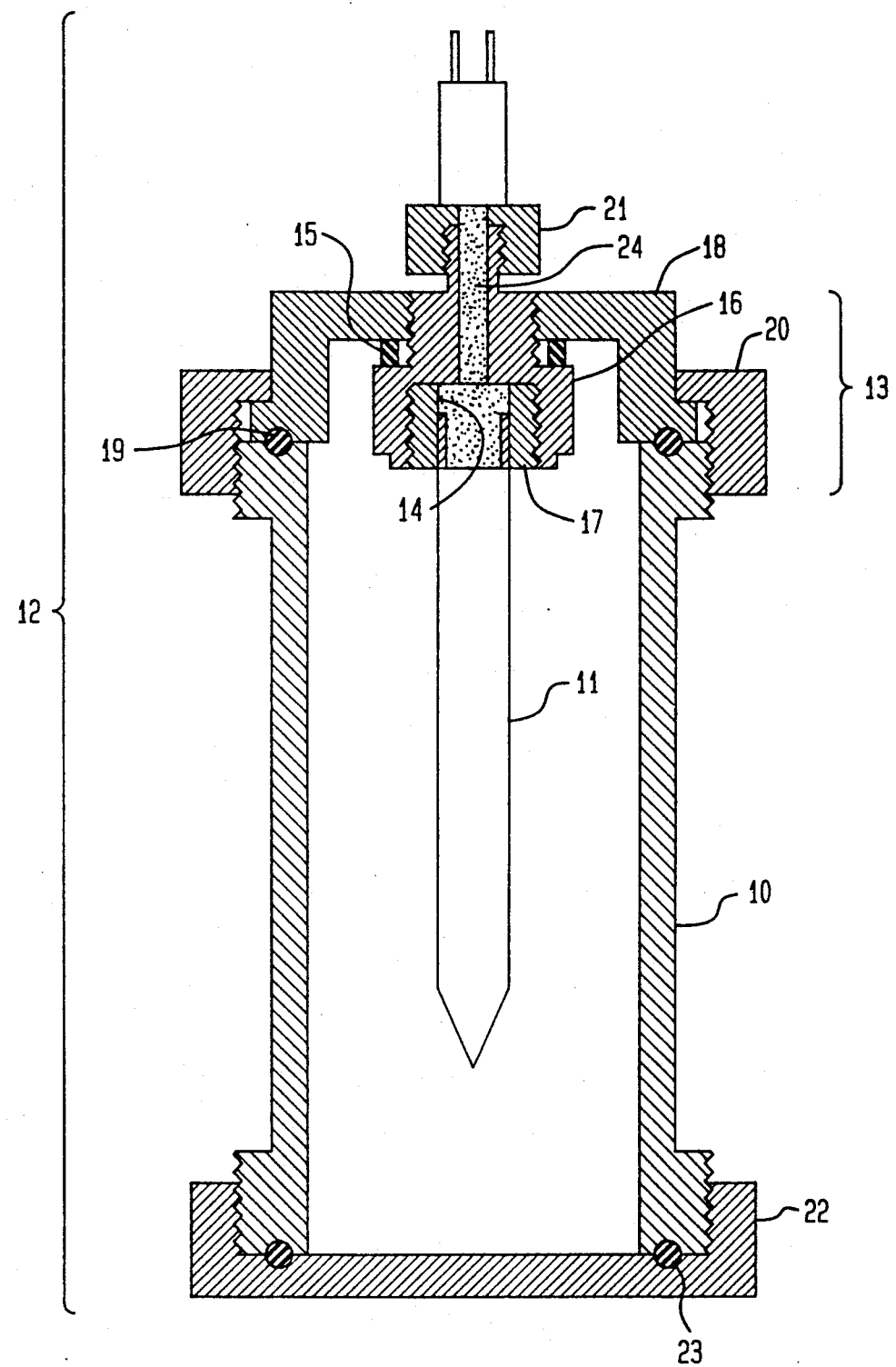
FIG. 1 is a cross sectional diagram of a sample holder and thermal probe assembly that are useful for moisture content measurements of liquid or semi-solid materials in accordance with the present invention.

It has been found that the moisture content of food materials can be indirectly measured, as a function of certain temperature related parameters, with sufficient precision to be useful for food processing purposes. Similar indirect measurement could be useful as to moisture content in other materials as well. The moisture content measuring method disclosed herein is advantageously based upon use of an improved form of a transient heat flow procedure utilizing a line heat source. In that transient heat flow procedure, heat at a predetermined level is applied for a predetermined time interval [i.e., a predetermined quantity of heat] to a sample of material. The heat is typically applied by way of an electric heater wire in a probe that has been placed in the sample. The probe also includes an electrical element for sensing temperature. Heretofore, the temperature measurements have been used to calculate a temperature characteristic for the material, that characteristic being expressed as temperature rise versus natural-logarithm-of-heating-time. The slope is determined and from that, with certain calibration adjustments, the thermal conductivity has been determined. This much, without improvements described herein, has been shown, for example, in the aforementioned Hooper et al. paper.

A method disclosed herein, and utilizing the improved procedure, has been found to be useful for correlating the heat transfer rate of a material with the moisture content of the material as long as temperature measurements are accomplished with a predetermined accuracy and as long as heat transfer from the line heat source is confined substantially to the sample material to render those temperature measurements meaningful. The predetermined accuracy is usually determined by particular food processing plant conditions. The foregoing improved method, hereinafter called simply "the method," and the apparatus for carrying it out are described below and have been found to meet the aforementioned requirements for food processing-related measurements, namely, high temperature tolerance, short time to make a moisture content measurement of a sample, ease of calibration, and substantially no contamination between sensor and food system. In addition, the method lends itself to the accomplishment of moisture content measurements in on-line, food processing applications where the material being processed has a substantially uniform temperature distribution.

Food material temperature parameters which have been found to be representative of moisture content are comprised in the slope of the thermal response of the material, namely the temperature-difference versus natural-logarithm-of-heating-time response. Logarithms using a different base also can be employed. In particular, a regression equation can be obtained by any known linear regression analysis technique and which comprises a polynomial in which moisture content of a sample of the material is expressed as a function both of (a) a slope, which is approximately the maximum slope, of that response of the sample and (b) a temperature parameter related to the sample temperature at the start of heat application. One such parameter is the mean temperature during the heating time interval over which that maximum slope is determined, that mean temperature necessarily being dependent upon the initial temperature at the start of heat application. Unless otherwise indicated for certain cases to be discussed, this mean temperature is the one used herein in the regression equation.

The aforementioned regression equation is meaningful, i.e., produces moisture content with sufficient reliable precision for food processing purposes, only if (a) the underlying temperature measurements are made with corresponding precision and (b) heat transfer from the heat source is limited substantially to the sample material. The requisite precision is determined by the type of product involved and by processing plant conditions. For example, a plant operating at a given efficiency level will require corresponding measurement precision for moisture content controls included in a processing function.

Also, it has been found that certain stabilization relationships must be established. For example, in order that the line heat source concept be validly employed, it is necessary that the heat application and temperature sensing function be accomplished with the least possible intrusion of their own physical dimensions upon the transfer process. It is also necessary that there be a relatively uniform thermal contact conductance, between the heat application apparatus, i.e., the probe, and the sample material.

FIG. 1 illustrates in a cross sectional view one embodiment of a sample holder and thermal probe assembly 12 for use in measuring moisture content of predetermined materials as a function of the aforementioned temperature parameters of the material. This holder assembly comprises a holder 10 and a thermal probe 11, and it is primarily useful for measurements on liquids, e.g., gelatinized starch solutions, or semi-solids such as cheese sauce. Probe 11 advantageously includes an electrically energizable heater and a suitable, electrically responsive, temperature sensing element, as will be subsequently described. Holder 10 is fabricated of a material, such as aluminum, which neither affects nor is affected by the chemical composition of a sample material being measured. The holder material also has a heat transfer ability [thermal conductivity] which is much higher than the thermal conductivity of materials for which it is expected that moisture content will be measured. This assures that the holder and any contained sample material will relatively rapidly attain temperature equilibrium. Holder 10 is illustratively of circular cylindrical transverse cross section and is provided with sealing covers at each end, as will be subsequently described, to prevent the escape of moisture which may otherwise evaporate from a contained sample material [not shown] during sample heating required for measurements.

A first cover 13 for holder 10 is an assembly of several concentric parts which accomplish sealing of one end of the holder 10 and also make it possible to install the probe 11 in the holder without the necessity for twisting electric circuit connections. If twisting were required for installation, it would both tangle electrical circuit connections to the probe and raise a substantial risk that nonuniform thermal contact conductance would be created between the sample material within holder 10 and the probe 11. A central part 16 of cover 13 is provided to secure the probe 11 and includes a lower, inverted cup portion having internal threads to receive and hold a hollow, cylindrical, thermal, insulating sleeve 17 fabricated of a thermal insulating material, such as that commercially available under the trade name TEFLON of E. I. du Pont de Nemours & Company. The probe 11 is inserted into sleeve 17 as will be described. Central part 16 also includes a first, externally threaded, upper portion which is secured into a central, internally threaded, intermediate part, or cap, 18 which is provided with an outwardly radially extending flange. That flange mates with the upper edge of the holder 10, with an intermediate O-ring 19. The flange also provides externally an annular seat to be engaged by an inwardly extending annular flange of an outer part, or clamping ring, 20. Clamping ring 20 includes internal threads below its aforementioned flange for engaging external threads on the outer surface of the upper portion of the exterior surface of holder 10.

Probe 11 is installed into holder 10 by first screwing the insulating sleeve 17 into central part 16. Then probe 11 is inserted, with a friction fit, into sleeve 17 far enough to position it firmly but not far enough to touch the lower surface of central part 16. The space 14 above the upper end of probe 11 and the remaining upper portion of the central opening through the part 16 is then filled with a suitable potting material such as epoxy 24. Both epoxy and TEFLON have much lower thermal conductivities than do probe 11 and holder 10 and its covers. This arrangement mechanically secures probe 11 into the central part 16 but establishes thermal insulation between them because of the insulating sleeve 17 and the aforementioned space 14 above probe 11 and which is now filled with epoxy 24. Cap 18 is screwed onto the central part 16 with a sealing gasket 15 between them.

A connector 21 is screwed onto a second threaded part of central part 16 which protrudes from cap 18. The probe heater and sensing circuit leads extend therefrom into a connector plug 25 to be connected to appropriate cable leads as will be described. Next, the cap 18 is placed on top of the holder 10, and the clamping ring 20 is screwed onto holder 10 to clamp and seal cap 18 onto holder 10.

A second cover 22 is provided for the lower end of the holder 10 and is screwed into place, with an intermediate O-ring 23, after sample material [not shown] has been loaded into holder 10.

When a sample material is to be measured, holder 10, with first cover assembly 13 and probe 11 in place, is inverted. Sample material is loaded, before placement of cover 22, slowly enough that it can be visually monitored. Any tendency for an air space to form will be observed and corrected by an operator so that the loading is accomplished without significant air spaces in the material as loaded, and particularly no air spaces at the interface between the sample material and the outer surface of probe 11. Such air spaces are to be avoided because air usually has a significantly lower thermal conductivity than the sample material and would distort the rate of heat transfer from the probe to the sample material. Cover 22 is then replaced and measurements conducted while the holder 10 remains in the inverted position so that there will be no shifting of the sample material within the holder from the loaded condition with its assured uniformity of interface contact with probe 11.

When a test has been completed, it is usually necessary to remove only the second cover 22, clear sample material out of the holder, and load a new sample. Such operations can be accomplished relatively quickly compared to prior arrangements in which it is necessary to remove the probe and its mounting cover in order to clear and reload the holder.

Figure 2:
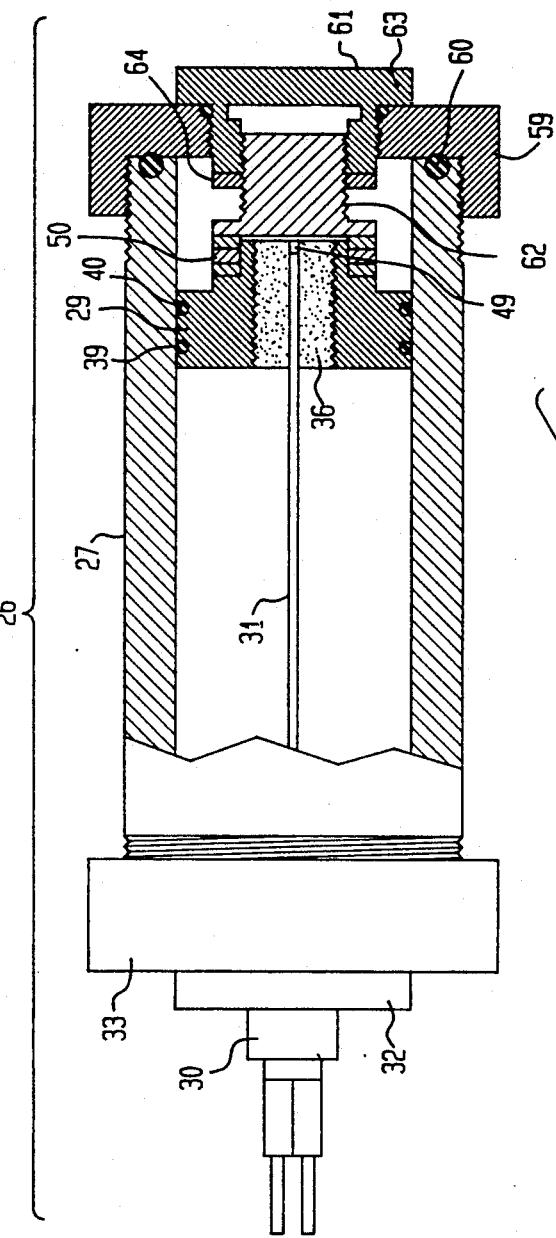
FIG. 2 is a cross sectional diagram of a sample holder and thermal probe assembly that are useful for moisture content measurements of powdered or other granular materials in accordance with the present invention.

FIG. 2 illustrates a second embodiment of a sample holder assembly 26 which is primarily useful for powdered, e.g., granular, sample materials. Of course, this holder assembly can be used for moisture content measurements on other types of materials as well. The assembly 26 includes means for compacting a predetermined weight of sample material to a predetermined volume; so the density of the material is then known and remains constant during measurements. Thus, the effect of variable density is substantially eliminated from measurements.

Sample holder assembly 26 comprises a hollow cylindrical holder 27 having, illustratively, a circular transverse cross section. A piston 29 is located in the right-hand (as illustrated) portion of the interior of holder 27. This piston can be driven toward the longitudinal center of holder 27 to achieve the aforementioned predetermined internal volume between the internal faces of the piston 29 and the probe end of holder 27.

A probe connector 30 is provided as before for making electrical connections to a probe 31, which is essentially the same as the probe 11 in FIG. 1, i.e., thermal insulation [not shown] is provided between probe 31 and the parts of the cover assembly in which it is mounted. The probe 31 is substantially longer than probe 11 for reasons that will shortly be explained. Connector 30 is shown mounted flush against intermediate cap 32. Cap 32, clamping ring 33, and probe connector 30 are assembled together and then assembled to holder 27 before it is loaded with sample material. This assembling operation is accomplished, in a manner similar to that already described for the cover assembly 13 in FIG. 1, and without twisting electric circuit leads [not shown] extending from connector 30.

Piston 29, at the right-hand end of holder 27, is provided with two O-rings 39 and 40 to seal against sample material leakage from the predetermined volume region at the left of piston 29. A thermally insulating sleeve 36, e.g., of TEFLON insulating material, is threaded into the interior of piston 29 and has its central longitudinal axis coincident with that of the piston. A narrow hole 49 is provided along the central longitudinal axis, and through the full length, of sleeve 36. Hole 49 has a diameter only large enough to accommodate probe 31 with enough clearance for smooth, unlubricated, relative movement between probe 31 and sleeve 36. This type of engagement assures that probe 31 remains substantially on the central longitudinal axis of holder 27 during compacting of sample material.

Piston 29 has a reduced-diameter portion on its back portion to form an annular seat on the back face of the piston. That reduced diameter portion receives and centers a thrust bearing assembly 50 [shown in greater detail in FIG. 3].

Figure 3:
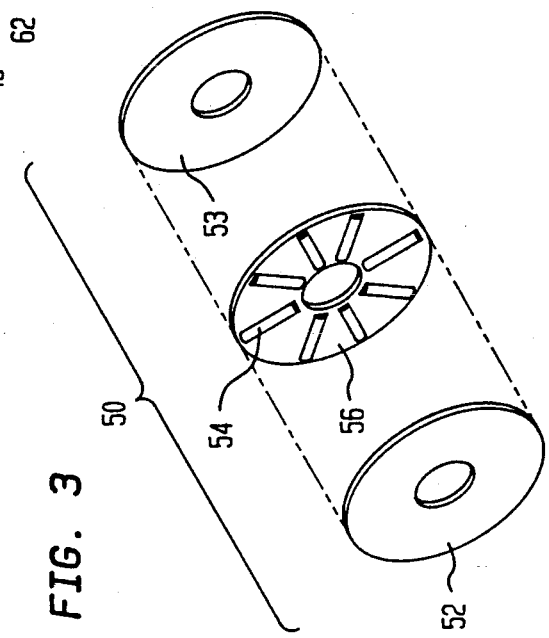
FIG. 3 is an exploded view of a thrust bearing assembly employed in the sample holder of FIG. 2.

Referring for the moment to FIG. 3, the thrust bearing assembly 50 includes first and second bearing washers 52 and 53 and a central race washer 56 which supports plural, radial, roller bearings, e.g., 54, rotatably mounted within its body, each having a diameter slightly greater than the thickness of the washer 56 supporting them. Those roller bearings transfer longitudinal force between washers 52 and 53 while permitting those washers to rotate relative to one another about the longitudinal axis of piston 29 and holder 27. When the thrust bearing assembly is in place on piston 29 in FIG. 2, its washer 52 is in contact with the annular seat on the back of piston 29, and its washer 53 extends somewhat beyond, i.e., to the right of, the right-hand end of the reduced diameter portion of the piston 29.

In FIG. 2 a right-hand cover 59 is threaded onto the holder 27 with a sealing O-ring 60 between them. This cover includes arrangements for mechanically driving the piston 29. A micro-displacement adjuster is provided and includes both an outer part 61 which is threaded into the center of the cover 59 and an inner part 62 which is threaded into a central cylindrical recess in the outer part 61. A relatively fine thread pitch [e.g., eleven threads per centimeter (cm)] is employed to assure adequate mechanical advantage for accomplishing smooth volume adjustments. The parts 61 and 62 are assembled to a predetermined degree of telescoping relationship and then locked into that relationship by any suitable means such as a lock nut 64.

Before moisture content measurements are accomplished with the sample holder of FIG. 2, its internal volume in the fully compressed [i.e. left-most] position of piston 29 is determined as the predetermined volume [V] needed for sample density determinations. That fully compressed position is advantageously the piston position realized when adjuster parts 61 and 62 have been locked into a known telescoping relationship and outer part 61 has been turned into cap 59 until it is flush against the cap. Then the predetermined volume is the interior volume to the left of piston 29 and is easily determined from the known dimensions of the parts of the holder. This determination is even more easily made if a blocking washer [not shown] is placed against the inner end of the central part of the left-hand cover assembly so that the holder interior volume is the volume of a regular cylinder less the volume of the probe portion extending through that cylinder. The blocking washer is left in place during sample moisture content measurements as well.

For mechanical operation of the holder of FIG. 2, the probe 31 and the left-hand cover assembly [including the connector 30, cap 32, and clamping ring 33] are assembled onto the holder 27 as previously described. A sample [not shown] of a material to be measured for moisture content is loaded into the interior of holder 27, also as previously described for loading the holder of FIG. 1, i.e., while visually monitoring the loading to assure substantially uniform contact between the sample material and the outer surface of probe 31. This sample is, for example, a powdered or granular material having a predetermined volume somewhat greater than the aforementioned volume V of the illustrated free space to the left of piston 29. That sample also has a predetermined weight [W].

Thrust bearing assembly 50 and piston 29 are then inserted into holder 27, and the cover 59 [with its adjuster parts 61 and 62 retracted] is assembled onto the holder 27. Adjuster outer part 61 is turned into holder 27 by hand, or with the aid a suitable wrench, thereby driving piston 29 toward the left to compress the sample material and any air trapped inside holder 27 during the assembling of the various parts. The driving force is applied to piston 29 through the thrust bearing assembly 50 without inner part 62 ever contacting piston 29. When the outer part flange 63 engages the outer surface of cover 59, it is known that the holder predetermined internal volume V used as a guide in setting up the telescoping relationship of adjuster parts 61 and 62, has been achieved. Since the volume V and weight W of the sample are now established and fixed, the density of the sample is fixed and will remain the same throughout the measurements necessary for determining moisture content. As previously pointed out, constant density is desirable both during individual moisture content measurements and from sample to sample of a group of samples of a given material, especially powdered or granular materials.

Different values for the predetermined volume V of compacted sample material can be achieved by resetting the telescopic relationship between adjuster parts 61 and 62. Such different volume values also can be obtained by operating adjuster outer part 61 to different calibrated positions of less than complete insertion into the cover 59.

It has been found that small volumes of air that are trapped inside holder 27 when piston 29 is inserted after sample loading have a negligible effect upon the moisture content measurements. It also has been found that as long as the aforementioned fine threads are employed there is a wide range of tolerance for different levels of torque applied during mechanical operation of the adjuster parts 61 and 62 without significantly impacting sample density or final moisture content measurements.

The sample holder of FIG. 2, with its adjuster and compacting piston, requires more set-up activities between tests than does the FIG. 1 embodiment. However, it provides the known density required for powders with accuracy sufficient to yield moisture content measurements that correlate with measurements made by the standard oven method.

Figure 4:
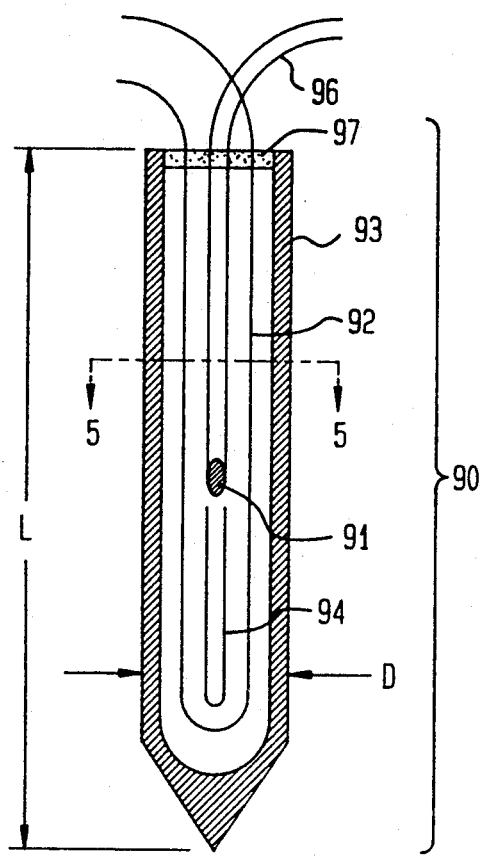
FIGS. 4 and 5 are cross sectional views of a thermocouple-based thermal probe that is useful in the sample holders of FIGS. 1 and 2.
Figure 6:
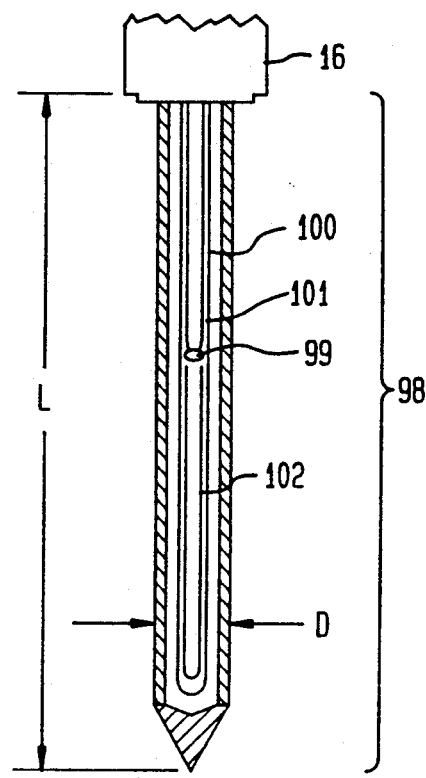
FIG. 6 is a cross sectional view of a thermistor-based thermal probe that is useful in the sample holders of FIGS. 1 and 2.
Figure 5:
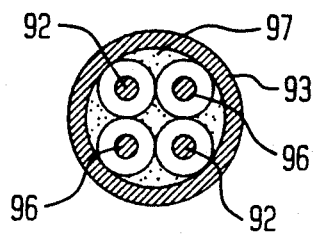

Thermal probes, such as the probes 11 and 31 in FIGS. 1 and 2, include an electrical heating wire (for providing controlled heat to the sample material through the probe) and an electrical, temperature sensing element (for indicating temperature changes in the sample material as a result of the heating). Thermocouple sensing elements and thermistor sensing elements have been employed in the present method. The thermocouple elements have been found to allow more rapid measurements than do the thermistor elements. However, the thermistor elements provide about an order of magnitude better resolution accuracy because they are more stable than are the thermocouple elements. In addition, thermistors can be employed over the full temperature range of about 30° C. to 150° C. presently of interest for food processing. However, it has been found that in the system illustrated, thermocouples are useful in only the portion of that range below 100° C. FIGS. 4-6 illustrate probe details for both thermocouple based and thermistor based probe embodiments.

It has been found that for making moisture content measurements in accordance with the method here disclosed, the directly measured temperature measurements must be made with a high degree of accuracy in the sense of accurately reflecting the true temperature of the material which is being measured so that the degree of heat diffusion into the sample material will be accurately reflected. To that end, it has been found further that a thermal probe which performs both sample heating and temperature sensing functions should present a thermal appearance which resembles as nearly as possible a line heat source, i.e., a source with the smallest practical diameter. This aspect is discussed in greater detail below.

FIG. 4 depicts a probe 90 of the type useful in sample holders of FIGS. 1 and 2 for making moisture content measurements. Probe 90 is a thermocouple probe, and it has certain features which have been found effective in giving the probe a substantially line-heat-source thermal appearance. Probe 90 includes a thermocouple junction 91 of electrically insulated constantan and copper wires 96 and an electrically insulated constantan heater wire 92. The thermocouple and heater wires are each illustratively of 40 gage wire, and they are encapsulated in a high thermal conductivity paste [not shown] within a stainless steel tubing 93. One such paste is the silicon paste TO-201 of Omega Engineering, Inc., of Stamford, Conn. Stainless steel usually does not react chemically with food materials. The thermal conductivity of the paste and of the tubing 93 are chosen to be much higher than that of the sample material which is to have its moisture content measured so that temperature monitored by a temperature sensor in probe 90 is an accurate representation of the sample material temperature at the probe-material contact location.

Junction 91 is located approximately midway along the length L of the probe. In addition, an open unconnected wire 94 is looped in the lower half of the probe below junction 91. The unconnected wire is provided so that, even though all probe components are made of high thermal conductivity materials compared to any sample material, the thermal appearance of the probe will be more nearly uniform along its length and thereby more nearly resemble a line heat source. Heater wire 92 is looped through substantially the entire length of the tubing 93. The ends of the heater wire 92 and of wires 96 connected to the junction 91 extend through an epoxy plug 97 in the top of the tubing 93 where they are passed through a central part [not shown] of a cover to a connector, such as the connectors 21 and 30 previously mentioned in FIGS. 1 and 2.

In order for moisture content measurements based upon use of a thermal probe to have the desired accuracy, temperature measurements should reflect as accurately as possible the extent of heat transfer from the probe to the sample material. This is desirable because methods usually employed for data reduction are based on a theoretical assumption that heat is transferred from a line heat source into an infinite body with negligible deviation from the heat diffusion pattern that would prevail in an infinite body. The probe and the enclosing sample holder have been proportioned to achieve that end without making the overall holder and probe assembly 12 so large that it is inconvenient to handle. That is, they are designed so that there will be an essentially uniform temperature distribution along the greatest practical extent of the length of the probe and so that during the maximum duration heating interval that is expected to be employed, for the highest thermal conductivity sample material that is expected to be measured, there will be essentially no change in the sample material temperature by the interior cylindrical surface of the holder. A sample holder of the type in FIG. 1 was found to meet these requirements when the internal diameter was made about 38 millimeters [mm] for making measurements on samples requiring up to about 200 milliamperes of heating current for up to about 300 seconds.

It has been found that probe 93 should have a length-to-diameter ratio L/D of at least 50 [rather than the usual ratio of about 25 which is more generally employed in probes for, e.g., thermal conductivity measurements]. This much larger L/D ratio exhibits nearly uniform temperature along the central half of the length of the probe and thereby further enhances the line-heat-source, thermal appearance of the probe. In one embodiment of a thermocouple probe, a probe diameter of 0.78 mm and a length of 40 mm were employed.

A probe tip spacing from the bottom of the sample holder must be sufficient to prevent disturbance of the heat diffusion pattern. That is the temperature distribution along the length of the probe should be approximately symmetrical about the center of the probe length, where the thermocouple sensor is located. For the probe embodiment just mentioned, a holder as in FIG. 1 was made long enough to provide at least 15 mm clearance between the probe tip and the bottom, i.e., bottom cover 22, of the holder to achieve that relationship. In practice, the holder was made substantially longer, i.e., an interior length of 100 mm, in order to accommodate alternatively a longer thermistor probe to be described below.

FIG. 5 is a cross sectional view of the probe of FIG. 4 taken at the lines 5, 5 in FIG. 4. This figure shows the insulated, heater and thermocouple wires in the silicon paste 97. That paste is employed to displace any air within the tubing 93 and thereby assure relatively uniformly high thermal conductivity throughout the probe 90. High temperature resistant insulation, e.g., TEFLON insulation, is used on the thermocouple and heater wires for electrical insulation. The insulation is in the form of a thin coating which is sufficient for electrical insulation purposes but does not significantly impede heat transfer.

FIG. 6 depicts a probe 98 of the type useful in sample holders of FIGS. 1 and 2 for making moisture content measurements. Probe 98 is a thermistor probe, and it has certain features which have been found effective in giving the probe a substantially line-heat-source thermal appearance. Probe 98 includes a looped heater wire 100 of the same type and configuration as the wire 92 in FIG. 4. A thermistor 99 is also included; and its electrical connection wires 101 extend up through a cover central part 16, or the like, as described in connection with FIG. 1. An open unconnected wire 102 is looped in the bottom half of the probe below thermistor 99 to improve the thermal profile, as described in connection with FIG. 4. In addition, the length-to-diameter ratio L/D of probe 98 was made greater than 60 to enhance further the line heat source appearance of the probe. Otherwise probe 98 is constructed in substantially the same way as the probe 90 just described in FIG. 4. In one embodiment, probe 98 included a stainless steel tube 80 mm in length and 1.27 mm in diameter. Stainless steel does not usually react with food materials. Both probes [FIGS. 4 and 6] are fitted into a mounting such as the central part 16 shown in FIG. 1.

Figure 7:
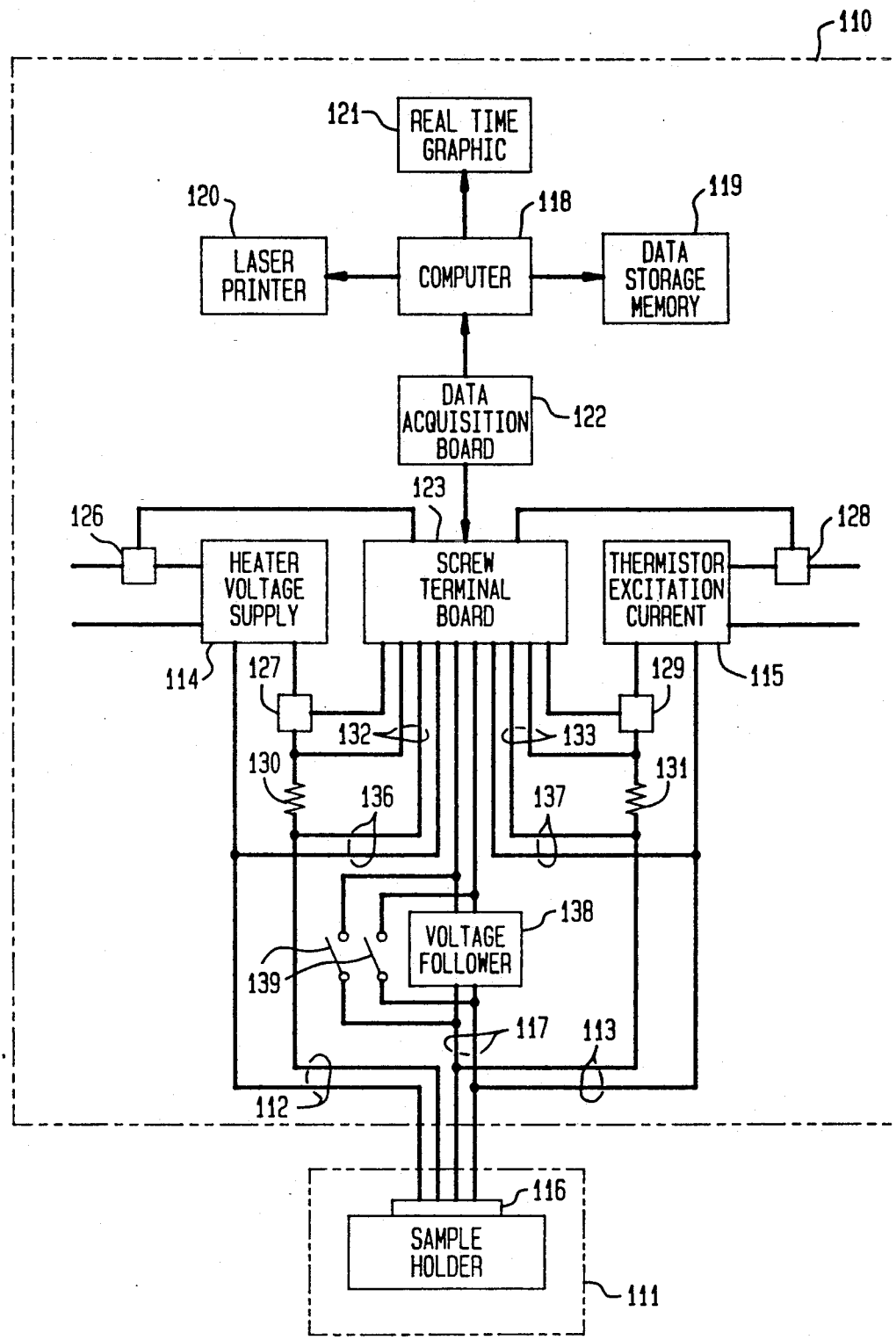
FIG. 7 is a block and line diagram of an automated control and data collection and processing system for making thermal probe measurements for moisture content determination.

In FIG. 7 is shown a simplified block and line diagram of a computer controlled, automatic, probe control and data collection and processing system which is useful in carrying out the moisture content measuring method described herein. This system differs from others of the type known in the art primarily as to several aspects incorporated to improve precision in control of the probe as well as providing for high speed operation for both measurement efficiency and minimizing modification, i.e., cooking, of—and evaporation from—the sample material during measurement operations. The improved system can operate with either a thermocouple probe or a thermistor probe. Included in the improved system are a high resolution data acquisition board, a high stability voltage supply for the probe heater, a precision current supply for a probe thermistor, and a switchable voltage follower for coupling voltages from a probe thermistor to the data acquisition board, all as will be further described below.

In FIG. 7, a sample holder and probe assembly 111 schematically represents either a discrete sample holder and probe of the type illustrated in FIG. 1 or FIG. 2 or a more general sample containing means such as a trough or conveyor or the like in a processing plant with a controlled environment. The assembly 111 is electrically coupled to the system 110 by two pairs of electric circuit leads. A first lead pair 112 couples a high-stability heater voltage supply 114 through a connector 116 to the probe heater wires in assembly 111. The voltage supply is able to maintain a preset heater voltage and current in ranges of zero to twenty volts and zero to ten amperes with less than 0.01% of load regulation and less than 10 millivolt peak-to-peak ripple and noise [20 Hertz to 20 megahertz] and 0-10 amperes with less than ±0.02% of load regulation and less than 33 milliamperes rms ripple and noise (20 Hertz to 20 megahertz]. The supply is able to switch current on or off in no more than 4 milliseconds without significant oscillation. Although such supplies are commercially available, they have not been heretofore used or necessary in thermal response measuring systems.

A second lead pair 117 is connected to couple the probe temperature sensing element, whether it be a thermocouple or a thermistor, to the data collecting and processing portions of system 110. A third lead pair 113 couples a precision excitation current supply 115 across the lead pair 117 for applying current through connector 116 in assembly 111 to a thermistor, when employed, in the probe of assembly 111. Supply 115 provides output current in a selectable range of zero to 100 milliamperes as a constant current source and maintains the selected current to within ±0.05% in spite of load (thermistor resistance) increases by factors of at least 140. Supply 115 is calibrated to produce its selectable outputs within 0.02% of the indicated range switch setting. Ripple and noise at any selectable output are no more than 200 nano-amperes rms and four micro-amperes peak-to-peak. Supply 115 also exhibits less than four milliseconds response time on a one milliampere range load transient recovery time.

System 110 is managed by an operator at the keyboard [not separately shown] of a personal computer 118. Data collection and processing to produce moisture content information are carried out in accordance with the method steps to be described. Apart from the method comprising those steps, and apart from the aforementioned system 110 improvements, the arrangement and composition of the hardware in system 110 is illustrative of various control and data collection and processing systems that could be employed and comprise no part of the present invention.

Computer 118 has cooperatively connected to it external memory 119 for data storage and an output device which is schematically represented by a laser printer 120 but which can be any appropriate computer output utilization means. Such utilization means can include, e.g., food processing system controls for regulating processing operations, in response to moisture content data determined by the measuring method described herein, to change moisture content in samples subsequently to be measured. A suitable real time graphics output device 121 can also be provided if desired. Computer 118 is programmed to execute a program defined by the aforementioned method steps, to be described, and which holds database information in an application software program. Collected and calculated data are held in the memory 119.

The aforementioned program for computer 118 is illustratively Labtech Notebook, version 6.0, produced by Laboratory Technologies Corporation, 400 Research Avenue, Wilmington, Mass. 01887. It controls functions such as the on/off timing for the probe heater and the timing for taking data, i.e., temperature, readings. The software also has the capability to connect its operation with other data manipulation software written in a different language from that used in Labtech Notebook, and such other software of a conventional nature was advantageously written in the Basic language for performing the data calculations necessary for carrying out the mentioned method steps. Illustrative calculations so performed include temperature differences, natural logarithm of heating time, slope of thermal response characteristic, mean temperature corresponding to a slope calculation, selection of the maximum of a set of values, and solution of a predetermined regression equation [to be discussed].

A data acquisition board 122 is controlled by computer 118 to issue appropriate control signals and collect data all by way of a screw terminal board 123. Solid state relays responsive to those signals are advantageously employed for actuating the various elements of the system 110 to assure precise actuation times and thereby minimize measurement errors that may arise due to relatively long switching times that characterize some mechanical switching devices. Thus, a relay 126 is controlled to actuate the voltage supply 114 for supplying heating current to the probe heater when a relay 127 closes the circuit including the lead pair 112 and a current sensing resistor 130. Similarly, a relay 128 actuates the low level current supply 115 for supplying excitation current to a probe thermistor when a relay 129 closes the circuit including lead pair 113 and a current sensing resistor 131. Resistors 130 and 131 have their respective end terminals connected through lead pairs 132 and 133, respectively, to board 123 for monitoring current application levels to a probe heater and to a thermistor. Branching circuits 136 and 137 extend from the heater lead pair 112 and the excitation lead pair 113, respectively, back to the terminal board 123 for providing circuit voltage information. Each branching circuit 136 and 137 shares a lead with one of the current sensing lead pairs 132 and 133, respectively.

Lead pair 117 provides temperature sensor [thermocouple or thermistor] voltage signals which are coupled to the screw terminal board 123 through an impedance matching voltage follower 138 when the sensor is a thermistor or through a manually operated bypass switch 139 when the sensor is a thermocouple. Impedance matching is necessary because the thermistor has calibrated resistance changes in response to temperature changes so it cannot have a low resistance voltage sensing circuit connected across it.

Turning now to a consideration of the moisture content measuring method utilizing the foregoing apparatus, it has been long known that there is a direct proportionality between thermal conductivity of a material and a slope of the material in the form of the temperature rise versus natural-logarithm-of-heating-time. It has also been known that thermal conductivity is influenced by moisture content. However, these relationships have not been harnessed previously to determine moisture content with sufficient precision to be useful in, e.g., food processing operations. It has now been found that if the aforementioned thermal response of temperature-difference versus natural-logarithm-of-heating-time of a sample of material is determined with suitable precision, the maximum slope of that response and a temperature related to the start-heating temperature can be substituted into a regression equation to yield the moisture content of the sample material to within approximately 2% absolute of moisture content of the same material determined by a standard method such as the standard oven method. That is, there is an absolute error range of about two percentage points between per cent moisture determined by the standard vacuum oven method and per cent moisture determined by the indirect measuring method described herein. The mean temperature difference of a time interval for which that maximum slope is determined is such a temperature related to the temperature at the start of sample heating. Such precision is useful, e.g., for many food processing operations involving plant efficiency and involving compliance with governmental regulations as to moisture content. The above indirect measuring method is described more fully below.

Figure 8:
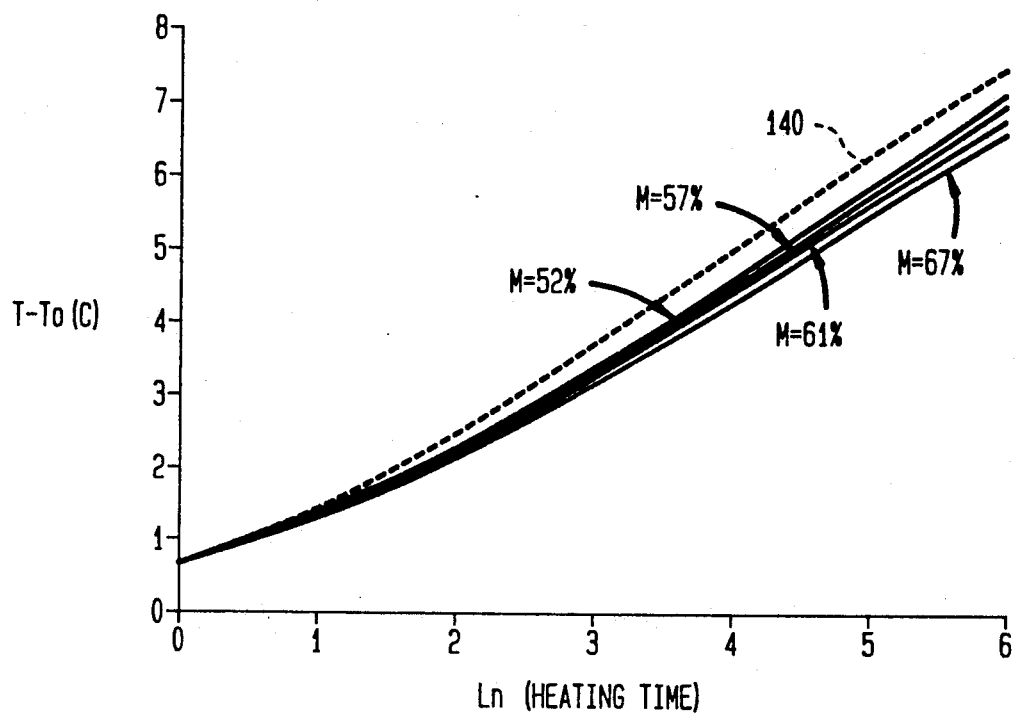
FIG. 8 is a family of thermal response curves illustrating certain aspects of the present invention.

FIG. 8 depicts thermal response curves [i.e., temperature-difference versus natural-logarithm-of-heating-time] for several samples of a given material [i.e., high amylopectin starch gel]. Each sample has a different per cent moisture content as indicated by the reference labels M=52%, M=57%, M=61%, and M=67%. The starting temperature $T_o$ for heating to generate the illustrated thermal responses was 90° C. in all four cases. The response curves were developed using a thermistor sensor in the probe. Temperature differences range form about 0.7° C. to 7° C., i.e., a final temperature of about 97° C., for the M=52% moisture content sample. The heating time interval shown is about 300 seconds, i.e., natural logarithms of heating time ranging from zero to about 5.7. Although the natural logarithm is advantageously employed, the common logarithm or a logarithm employing other suitable base can also be employed.

Several factors are evident from FIG. 8. One is that the slope of the response for the sample with 67% moisture is somewhat smaller than the slope of the sample with 52% moisture. Another is that the four responses all exhibit approximately continuous curvature from small slope near the beginning of heating, through a larger slope in the mid-length part of the heating interval. In some materials and in some applications convection effects (even inside the holder) cause an increase in the heat transfer rate toward the end of the heating interval which results in a smaller slope toward the end of the heating interval. A maximum slope segment usually lies some where in the mid-length part of the response. With such small slope differences for responses of samples with moisture content differences of about 15%, it is evident that it is difficult to distinguish slope differences for the fractions of per cent of moisture content that are necessary to be determined for food processing operations.

The foregoing factors are further complicated by the fact that thermal response characteristics change for different starting temperatures $T_o$. Not all food processing operations can be adequately characterized by a common starting temperature. The dashed-line curve 140 in FIG. 8 indicates the approximate effect of reducing the starting temperature $T_o$ from 90° C. to 50° C. for the 57% sample. That is, the 40° C. reduction in starting temperature causes a substantial increase in slope of the response.

A thermistor sensor was employed in the thermal probe used in developing the thermal responses for the samples indicated in FIG. 8. The curves each exhibits a mid-length, substantially straight, maximum slope portion. It has been found that the maximum slope part of the thermal response [i.e., temperature-difference versus natural-logarithm-of-heating-time] is one of the principal indicators of the moisture content of a material. Such slope information is not present in a simple temperature versus heating time response characteristic. Another principal indicator of moisture content is, as mentioned above, the starting temperature for the heating interval in the transient heat flow procedure. These two indicators are employed, as described below, to determine the moisture content of a sample material.

It has been discovered that moisture content can be determined, with the requisite precision from thermal response characteristic data such as those presented in FIG. 8. This is accomplished by using a regression equation for correlating the moisture content to the thermal response slope and temperature for a material of interest and for a probe type, e.g., thermocouple based or thermistor based, the equation being dependent on the material and the probe type.

The technique for developing a regression equation is well known once it has been determined what independent variables must be taken into consideration in order to produce an equation that will yield dependent variable values with sufficiently close correlation to physical actuality to be useful, e.g., for food processing operations. In spite of the fact that it is believed that there has been a long standing need to determine moisture content quickly and conveniently, there has not been developed heretofore a suitable regression equation.

Such an equation for a particular material of interest, and for a particular probe type, is developed by conducting a series of experiments using typical samples covering the entire range of temperature and moisture content of interest. Those experiments utilize one of the well known standard moisture content determining methods, such as the so called vacuum oven method, which is sometimes designated the A.O.A.C. 1990 method of the Association of Official Analytical Chemists, Washington, D.C. Such standard methods are readily capable of determining moisture content to the nearest one-hundredth of a per cent; but, as previously observed, long times [i.e., measured in hours] are required to measure the moisture content of each sample. In those experiments the thermal response of each sample is also determined using the same probe type which will be employed for later testing unknown samples and the same analysis method for determining thermal response maximum slope. Data collected in those experiments comprises a database. That database is analyzed to develop a regression equation for moisture content in terms of slope of the thermal response of the material and of a temperature which is a function of the initial temperature of that thermal response. One form of computer software that has been found to be suitable for performing such a database analysis, and which runs on a mainframe computer [not shown], is called SAS, version 5, produced by SAS Institute, Inc., Box 8000, Cary, N.C. 27511-8000.

An illustrative equation is shown below for high amylopectin starch gel and obtained using a thermistor probe. The maximum slope method [to be described below in connection with FIG. 9] was applied to obtain the slope values of the thermal response portion of the underlying regression analysis for the sample starch gels. The moisture content data portion of the regression analysis for the same gels was determined by the standard vacuum oven method. The following equation [A] was obtained through the regression analysis of the starch gel data obtained as above:

$$M = 254.4254 - 136.8415 S - 0.09656 T S^3 \qquad [A]$$

where M is moisture content [wet basis], S is maximum slope [C.°], and T is the temperature which is a function of the initial temperature, preferably the mean temperature of the maximum slope portion of the thermal response heating interval. The regression correlation coefficient for equation [A] is 0.9953.

The following Table illustrates comparative results of moisture content determinations for seven samples of the aforementioned high amylopectin starch gel of initially unknown moisture content and tested at four different starting temperatures. In these determinations, each sample was divided into two parts. Moisture content for one part was determined by the foregoing method of the present invention [M% Est] utilizing a thermistor sensor and the maximum-slope method for evaluating the thermal response measurement data, and moisture content for the other part of each sample was determined by the aforementioned standard oven method [M% Oven]. "Exp. S" is the maximum slope of the thermal response of the sample determined as above described. "Exp. T (°C.)" is the initial temperature of the gel. "|Error|" is the absolute value of the difference between the moisture content values determined by the two methods.

TABLE

| Exp. S | Exp. T (°C.) | M % Est. | M % Oven | |Error| |
|---|---|---|---|---|
| 1.2754 | 80 | 63.9 | 63.8 | 0.1 |
| 1.2609 | 90 | 64.5 | 63.8 | 0.7 |
| 1.3165 | 90 | 54.4 | 54.9 | 0.5 |
| 1.2695 | 80 | 64.9 | 65.9 | 1.0 |
| 1.2438 | 100 | 65.6 | 65.9 | 0.3 |
| 1.2852 | 100 | 58.1 | 57.5 | 0.6 |
| 1.2707 | 110 | 58.8 | 57.5 | 1.2 |

The foregoing Table shows slope determination to four significant decimal places, and moisture content determined with absolute error less than 2%, i.e. M% Est and M% Oven differed by less than two percentage points.

The test time, to collect sample thermal response data in the above experimental verification data table and make all computations to find moisture content, for seven samples required about 120 seconds per sample.

Similarly, equation and data for high amylopectin powder samples of initially unknown moisture content were determined, again using a thermistor sensor. In this case the maximum-$R^2$ method of maximum slope determination, instead of the specific maximum slope method, was used to find thermal response slopes to be employed for development of the regression equation. This alternate method of slope determination, which is faster than the maximum-slope method, was employed since the powder to be measured has a low thermal conductivity; and so maximum-slope method would have required a considerably longer time to complete measurements for a single sample. Such a long heating interval could produce at least initial phases of material decomposition, or "cooking," and result in unreliable thermal response data. The regression equation for high amylopectin starch powder is:

$$M = 108.5716 + 0.1602T - 23.4674S + 1.4257S^2 \quad [B]$$

The $R^2$ regression correlation coefficient for the above coefficient determinations was 0.9899.

In a making a typical moisture content measurement on a sample material having an unknown moisture content, a thermistor temperature sensor is employed. Temperature measurements are made at approximately 0.2-second intervals throughout the sample heating time of, e.g., 150 seconds. Thermal response of temperature-difference versus natural-logarithm-of-heating-time is determined by calculating for each currently measured temperature data point both the temperature difference with respect to the initial temperature and the natural logarithm of the heating time from the time of the initial temperature measurement to the time of the current temperature measurement. In effect, the thermal response characteristic is divided into plural segments of substantially equal logarithm-of-heating-time values. Slope of the thermal response curve embodying the measurement data is calculated for each successive 2-second interval, i.e., each of those segments, during the heating interval.

Figure 9:
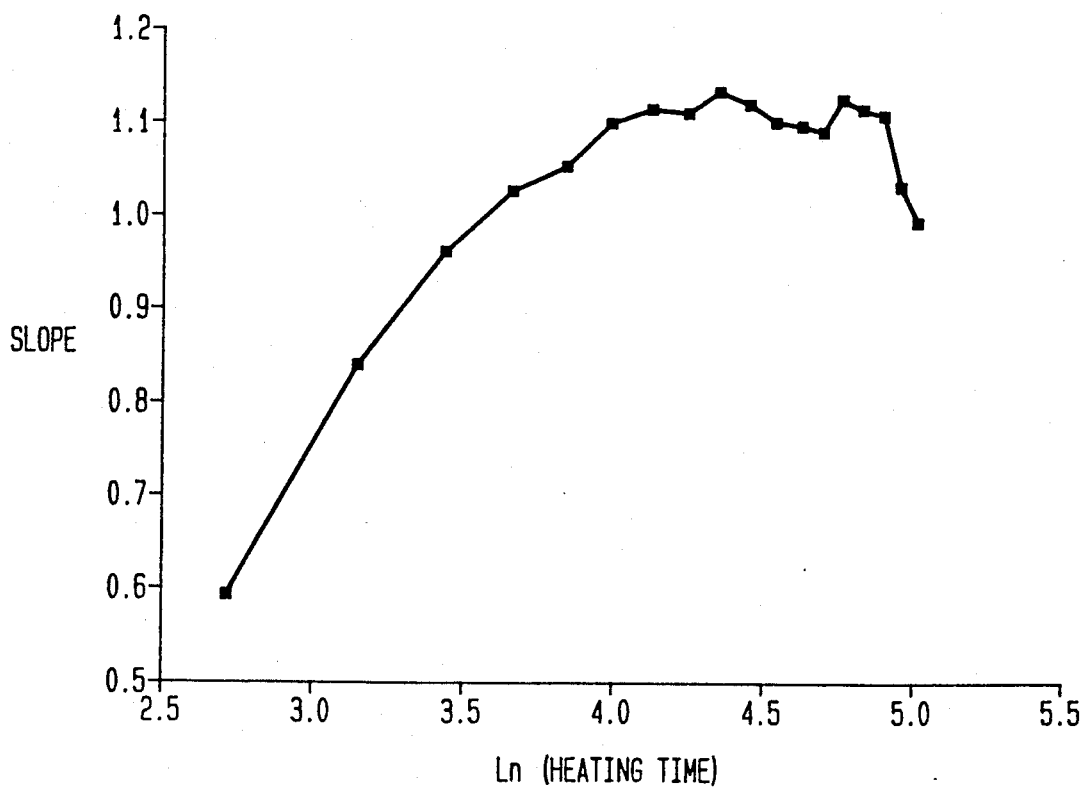
FIG. 9 is a slope versus natural-logarithm-of-heating-time graph illustrating one way for determining maximum slope of a thermal response curve.

Next the maximum value among all of the slope values so calculated is determined. FIG. 9 is a plot of such slope values versus natural logarithm of heating time for the M=57% curve in FIG. 8. FIG. 9 shows that the maximum slope for the illustrative sample test run occurred at about $\ln(t) = 4.4$, or at about 82 seconds, with a slope of about 1.1. Note that although the thermal response curves of FIG. 8 appear approximately straight at their right-hand ends, the maximum-slope determination shows that they do experience some reduction in slope toward the end of the heating interval.

The mean temperature difference is calculated over the 2-second interval for which the maximum slope was calculated. Finally, that maximum slope value and the corresponding mean temperature are substituted into the regression equation for the material, e.g., the aforementioned equation [A], to obtain the sample moisture content.

It is preferred to utilize a thermistor based thermal probe and to utilize the maximum-slope technique just described for determining the slope values in developing a regression equation because this probe produces appropriately precise results without requiring a special calibration procedure. However, in some applications it is convenient to employ a thermocouple based probe combined with the maximum-$R^2$ method of thermal response data analysis because a faster response time can be realized. The following is an equation for the use of the thermocouple based probe in the high amylopectin gel case:

$$M = 74.0868 + [-6.2610 + 20.7592S - 17.0094S^2]T + [0.0383 + 0.0892S^2 - 0.1178S]T^2. \quad [C]$$

Equation [C] is considerably different from the thermistor based probe equations [A] and [B] because of stronger interaction between the thermocouple-probe-determined slope and temperature. A thermocouple may be employed for faster determinations at temperatures below 100° C. in the particular illustrative apparatus environment and with a lower level of precision. The temperature limit is believed to result from apparatus interactions in the illustrative apparatus. The precision limitation results from the fact that the thermocouple exhibits much less temperature stability around a given constant temperature than does the thermistor. That lower stability limits temperature measurement resolution and prevents employment of the maximum slope method for determining slope of the thermal response. However, it is necessary to adjust the slope values determined from the measured thermal response of the sample material by a ratio of [a] thermal conductivity determined from the measured slope of the sample thermal response to [b] thermal conductivity of the same material as determined from a standard Heat Transfer Handbook. This slope adjustment ratio is necessary to account for the fact that the thermocouple probe is not a theoretically perfect line heat source. The thermistor probe also is not a theoretically perfect line heat source; but its finer measurement resolution makes use of the maximum-slope analysis method possible; and that method is, in effect, self calibrating for the lack of theoretical perfection in the probe.

For the convenience of the reader, there is presented here a brief discussion of the maximum-$R^2$ method of data analysis. It has been mentioned that in some applications it is more convenient to utilize a maximum-$R^2$ method of data analysis, rather than a maximum-slope method. One such application is the case of measurements involving high amylopectin starch powder, and another is the case of employment of a thermocouple based thermal probe. In those applications, the data to be analyzed is the thermal response of a material sample to determine the maximum slope of the thermal response. Such determination is made both for samples of known moisture content in the experiments in which a regression equation is developed and subsequently for samples of unknown moisture content to obtain slope and temperature values for use in that equation to determine moisture content.

In the cases in which maximum-$R^2$ data analysis is employed, a thermal response determination run is carried out over a shorter heating time interval than would be the case were the maximum-slope analysis method being employed. Certain final response data points based on final temperature measurements of the run are discarded, because they have been found to include run-end transient values that are not reliable; and the remaining final temperature value, called the last temperature $T_L$, is used in the data analysis for slope determination. Slope is then determined for the remaining response segment from initial temperature $T_0$ to $T_L$, and its regression correlation coefficient $R^2$ is determined. Then a slope is determined for a smaller segment of the response from a temperature $T_I$ to $T_L$ and its corresponding $R^2$ determined, usually producing a somewhat larger value of $R^2$. This step is repeated for successively smaller response segments and producing successively larger $R^2$ values either until a maximum value is determined or until a value is determined which is at least as large as a predetermined value. That predetermined value of $R^2$ is one which had previously been determined to be sufficiently large that the corresponding response slope would produce, in the corresponding regression equation, a moisture content value that adequately corresponds to actual physical conditions for the material processing purpose under consideration.

Each food type material, and each other type of material, that it may be necessary to test for moisture content will generally have its own regression equation for a particular probe type [e.g., thermocouple or thermistor based probe]. When the material type of a sample of unknown moisture content is identified, an operator inputs a command to the computer 118 in FIG. 7 for that type of material, corresponding temperature sensor type, and slope determination method to engage the corresponding database and regression equation. Once the appropriate sample holder and probe have been assembled, and the material sample loaded into the holder and sealed therein, the loaded sample holder is stabilized at a predetermined starting temperature which is suitable for the material. It is noted, however, that the stabilization step is not required for a sample already having a uniform temperature distribution, e.g., a sample from a material flow stream in a processing plant having controlled atmospheric conditions and in which the flowing material already has its temperature controlled to be the same as the local atmospheric [room] temperature.

When the operator inputs a Start command to the computer 118, measurement begins. That is, the probe heater is turned on at the predetermined level and for the predetermined heating time interval. If a thermistor probe is in use, it is energized at the same time. Measurements of sample material temperature are collected at each predetermined successive data collection time instant throughout the heating interval. Those temperature data are processed to obtain the thermal response parameters of the sample, e.g., the slope determined by either the maximum-$R^2$ or the maximum-slope method as appropriate to the probe and sample material. Also determined is the sample temperature, e.g., for maximum-slope data analysis, the mean temperature corresponding to the portion of the heating interval encompassing the maximum slope portion of the response. For maximum-$R^2$ data analysis the temperature $T_0$ is used as the sample temperature. Thereafter, the regression equation is solved for the per cent moisture as a function of both maximum slope and that mean temperature.

Although the invention has been described using particular illustrative structures and method steps, other arrangements which will be obvious to those skilled in the art are included within the spirit and scope of the invention as set forth in the following claims.

What is claimed is:

1. A moisture content measuring method for indirectly measuring the moisture content of a sample of material of a predetermined type, the method comprising the steps of:

developing a temperature-difference versus natural-logarithm-of-heating-time thermal response characteristic for said sample by a transient heat flow procedure starting at a predetermined initial temperature $T_0$ determining the maximum slope of said response characteristic;

determining the mean sample temperature of a portion of said response characteristic having substantially only said maximum slope; and calculating said moisture content of said sample as a function of said maximum slope and said mean temperature.

2. The moisture content measuring method in accordance with claim 1 in which said developing step comprises the step of establishing a predetermined density of said sample by compressing said sample to a predetermined volume before initiating said transient heat flow procedure.

3. The moisture content measuring method in accordance with claim 1 in which said developing step comprises:

enclosing said sample in a sample holder comprising:
  a hollow, generally cylindrical member having a much higher thermal conductivity than the thermal conductivity of said sample material;
  a thermal probe for both heating said sample and sensing temperature within said probe, said probe including a line heat source and at least one temperature sensing element enclosed in an encapsulating material within a tubing, said encapsulating material and said tubing both having a thermal conductivity that is much greater than the thermal conductivity of said sample material;
  first and second sealing covers secured to respective opposite ends of said cylindrical member to contain evaporants during moisture content measurements;
  said first cover including means, connected to one end of said probe, for removably mounting said probe to said cover, said tubing extending centrally into said holder when said probe and first cover are installed on said cylindrical member; and said removably mounting means comprising means for limiting heat transfer from said probe, when installed in said holder, to substantially only sample material in said holder, said limiting means comprising a cylindrical sleeve of thermal insulating material around said tubing at said one end of said probe for holding said tubing in a noncontacting relationship with respect to said first cover; and actuating said line heat source for a predetermined time period beginning at said time $T_0$, and at a predetermined actuation level, for developing said thermal response characteristic.

4. The moisture content measuring method in accordance with claim 3 in which in said enclosing step said probe has a length-to-diameter [L/D] ratio which is equal to or greater than fifty so substantially to present a thermal appearance in said sample material of a line heat source during said time period.

5. The moisture content measuring method in accordance with claim 3 in which in said enclosing step said sample holder interior dimensions and said probe exterior dimensions are so proportioned with respect to one another that during said predetermined period of actuation of said heat source there is substantially uniform temperature distribution along at least one-half of the length of said probe, which one-half of said length is approximately centrally located with respect to the center of said length; and there is substantially no temperature change at the inner surface of said holder during said period of actuation of said heat source.

6. The moisture content measuring method in accordance with claim 3 in which in said enclosing step, said thermal probe further comprises:

means for locating said sensing element within said tubing approximately midway along the length of said tubing, said locating means comprising a pair of electric circuit wires connected thereto; and an open, unconnected, electric circuit, wire loop within said tubing between a location adjacent to said sensor and an end of said tubing opposite to said one end thereof.

7. The moisture content measuring method in accordance with claim 3 in which said enclosing step includes a further step of:

compacting said sample material to a predetermined density; and said sample holder further comprises:

at least one piston within said cylindrical member; and means for movin said at least one piston longitudinally along the interior of said cylindrical member from one end of said cylindrical member adjacent to said second cover toward said first cover to reduce the interior volume of said cylindrical member between said piston and said first cover to a predetermined volume and thereby compact said sample material to a predetermined density.

8. The moisture content measuring method in accordance with claim 7 in which in said enclosing the step, said at least one piston further comprises:

a hole along a central longitudinal axis of said cylindrical member and opening onto said predetermined volume;

a thermally insulating sleeve in said hole, said sleeve having a central passage along the central longitudinal axis thereof, said passage having an inside diameter only slightly larger than the outside diameter of said probe, to receive a tip portion of said probe at an end of said tubing opposite said one end thereof during said compacting step for maintaining transverse centering of said probe during sample compacting by said at least one piston.

9. The moisture content measuring method in accordance with claim 7 in which in said enclosing step said sample holder means for moving comprises:

a driver extending through said second cover and in rotatable threaded engagement therewith for advancing said driver into the interior of said holder, along the longitudinal axis of said holder, during rotation of said driver in said threaded engagement, to drive said at least one piston toward the longitudinal center of said holder; and a rotational thrust bearing mounted on the back side of said at last one piston, toward said second cover, to receive said driver and absorb rotational motion thereof without transmitting the same to said at least one piston.

10. The moisture content measuring method in accordance with claim 9 in which in said enclosing step said driver further comprises:

a first driver part in rotatable threaded engagement with said second cover and having an exterior flange for the application of rotational force to move said first driver part into or out of said holder;

a second driver part in threaded engagement with said first driver part to enable adjustment of the overall length of said driver and thereby adjustment of the maximum extent of compacting movement of said at least one piston in said compacting step for thereby establishing said predetermined volume; and means for locking said first driver part and said second driver part in a selected degree of engagement.

11. A moisture content measuring method for indirectly measuring the moisture content of a sample of material of a predetermined type, the method comprising the steps of:

developing a regression equation for said material and relating moisture content as a function of the slope of a temperature-difference versus logarithm-of-heating-time response of said material during a predetermined heating time interval, and a first temperature which is a function of the material temperature $T_0$ at the start of said interval;

applying heat to an interior, substantially central, body portion of said sample at a predetermined rate;

measuring said thermal response of said sample during said predetermined heating time interval;

calculating the slope of said thermal response of said sample for a portion of said response having substantially maximum slope of all portions of said thermal response; and solving said equation for said moisture content of said sample as a function of said maximum slope and said first temperature.

12. The moisture content measuring method in accordance with claim 11 in which said developing step comprises developing a regression equation for said material and relating moisture content, the slope of a temperature-difference versus logarithm-of-heating-time response of said material during a predetermined heating time interval, and the mean sample temperature during said portion of maximum slope.

13. The moisture content measuring method in accordance with claim 11 in which said slope calculating step comprises:

selecting a maximum-$R^2$ portion of said characteristic of maximum slope as indicated by a best fitting regression line having a maximum $R^2$ regression correlation coefficient;

utilizing the slope of said maximum-$R^2$ portion of said characteristic as said maximum slope thereof; and utilizing said temperature $T_0$ as said first temperature.

14. The moisture content measuring method in accordance with claim 11 in which said slope calculating step comprises:

dividing said thermal response into plural segments of substantially equal logarithm-of-heating-time values;

determining the slope value of each of said segments;

selecting the maximum slope value among slope values of all of said segments as said maximum slope of said thermal response characteristic; and utilizing the mean sample temperature during said segment of said maximum slope value as said first temperature.

15. The moisture content measuring method in accordance with claim 11 in which a sealable sample holder is provided for said sample and having an externally controlled heat source centrally mounted in the interior thereof, and said measuring step comprises the steps of:

enclosing said sample in said sample holder and sealing said holder closed; and during said heat applying step, limiting heat transfer from said source to substantially only said sample material.

16. The moisture content measuring method in accordance with claim 15 in which said enclosing step further comprises:

loading said sample material into said sample holder while said heat source is in said sample holder; and monitoring said loading of said sample material to prevent formation of nonuniformities at an interface between said sample material and said heat source.

17. The moisture content measuring method in accordance with claim 15 in which said sample has a predetermined initial volume and a predetermined initial weight and said enclosing step further comprises the step of connecting said sample to a predetermined compacted volume, which is less than said initial volume thereof, after said loading of said sample into said container, whereby said sample has a predetermined density, corresponding to said predetermined weight and said predetermined compacted volume, during said measuring step.

18. Apparatus for measuring moisture content by internally heating a sample of material to produce temperature-representative electrical signals indicating the extent to which heat is transferred into said sample material and transforming those signals into a temperature-deference versus natural-logarithm-of-heating-time characteristic trace for the sample material from which moisture content of the sample material is determined, said apparatus comprising:

means for heating a substantially central interior region of said sample for a predetermined time at a predetermined rate of heat application;

means for producing electrical signals representing temperature within said sample adjacent to said heating means during said predetermined time; and computing means including a memory and programmed to sample periodically said electrical signals from said producing means during said predetermined time and store the signal samples, and sampling time information, and said memory as signal sample amplitude and sampling time information;

transform the stored signal sample amplitude and sampling time information into a temperature-difference versus natural-logarithm-of-heating-time thermal response characteristic for said sample material;

determine the maximum slope of said thermal response characteristic, said predetermined heating time being long enough to produce a segment of said characteristic having maximum slope but not long enough to heat substantially the radial periphery of said sample;

determine a first temperature which is a function of the sample material temperature $T_0$ at the start of said predetermined interval; and calculate the moisture content of said sample material as a function of said maximum slope and said first temperature.

19. The apparatus in accordance with claim 18 in which the computing means program step for calculating moisture content comprises solving a predetermined regression equation for material of the same type as said sample material, said regression equation expressing, for said sample material, moisture content as a function of said maximum slope and said first temperature.

20. The apparatus in accordance with claim 18 in which the computing means program step to determine maximum slope comprises said computing means being programmed to:

select a portion of said thermal response characteristic of maximum slope as indicated by a best fitting regression line having a maximum-$R^2$ regression correlation coefficient;

utilize the slope of said maximum-$R^2$ portion of said characteristic as said maximum slope thereof; and utilize said temperature $T_0$ as said first temperature.

21. The apparatus in accordance with claim 18 in which the computing means program step to determine maximum slope comprises said computing means being programmed to:

divide said thermal response characteristic into plural segments of substantially equal logarithm-of-heating-time values;

determine the slope value of each of said segments;

select the maximum slope value among slope values of all of said segments as said maximum slope of said thermal response characteristic; ad utilize the mean sample temperature during said segment of said maximum slope value as said first temperature.

22. The apparatus in accordance with claim 18 in which said heating means comprises:
a sample holder to contain said sample material;
a thermal probe mounted at one end of said sample holder and extending into said sample holder;
said thermal probe comprising an electric, line heat source and a temperature sensor adjacent to a central portion of the length of said line heat source and which sensor is a part of said means for producing temperature-representative electric signals; and
means for limiting heat transfer from said source to substantially only said sample material.

23. The apparatus in accordance with claim 22 in which said sample material is capable of assuming substantially different volumes for a given weight thereof and exhibits different thermal response characteristics for said different volumes, said sample has a predetermined initial volume and a predetermined initial weight, and said sample holder comprises
means for compacting said sample within said sample holder to a predetermined compacted volume, which is less than said initial volume thereof, whereby said sample has a predetermined density corresponding to said predetermined weight and said predetermined compacted volume.

24. The apparatus in accordance with claim 22 in which
portions of said sample holder and said thermal probe which contact said sample material during heating by said heating means are essentially nonreactive with said sample material.

* * * * *